United States Patent [19]

Smith, Jr.

[11] Patent Number: 5,120,403
[45] Date of Patent: Jun. 9, 1992

[54] METHOD FOR OPERATING A CATALYTIC DISTILLATION PROCESS

[75] Inventor: Lawrence A. Smith, Jr., Houston, Tex.

[73] Assignee: Chemical Research & Licensing Company, Houston, Tex.

[21] Appl. No.: 689,981

[22] Filed: Apr. 8, 1991

Related U.S. Application Data

[62] Division of Ser. No. 328,487, Mar. 23, 1989.

[51] Int. Cl.$^5$ .............................. B01D 3/42; B01J 8/02
[52] U.S. Cl. .......................................... 203/1; 203/2; 203/38; 203/DIG. 6; 422/106; 422/111; 422/112; 422/211; 568/697; 568/699
[58] Field of Search ................ 203/DIG. 6, 2, 1, 20, 203/29, 38, 99; 422/106, 111, 115, 190, 191, 211, 220, 112; 568/697, 699; 202/158, 264

[56] References Cited

U.S. PATENT DOCUMENTS

| | | | |
|---|---|---|---|
| 2,816,858 | 12/1957 | Walker | 203/2 |
| 3,011,956 | 12/1961 | Smith et al. | 203/20 |
| 3,027,307 | 3/1962 | Stoffer et al. | 203/20 |
| 3,401,092 | 9/1968 | Matta | 203/1 |
| 4,089,752 | 5/1978 | Hancock | 203/99 |
| 4,215,011 | 7/1980 | Smith, Jr. | 252/426 |
| 4,232,177 | 11/1980 | Smith, Jr. | 585/324 |
| 4,242,530 | 12/1980 | Smith, Jr. | 585/510 |
| 4,250,052 | 2/1981 | Smith, Jr. | 252/426 |
| 4,302,356 | 11/1981 | Smith, Jr. | 252/426 |
| 4,307,254 | 12/1981 | Smith, Jr. | 568/697 |
| 4,336,407 | 6/1982 | Smith, Jr. | 568/697 |
| 4,439,350 | 3/1984 | Jones, Jr. | 502/527 |
| 4,443,559 | 4/1984 | Smith, Jr. | 502/527 |
| 4,475,005 | 10/1984 | Paret | 568/647 |
| 4,482,775 | 11/1984 | Smith, Jr. | 585/671 |
| 4,550,012 | 10/1985 | Penick | 422/106 |
| 4,847,430 | 7/1989 | Quang et al. | 568/697 |
| 4,847,431 | 7/1989 | Nocca et al. | 568/197 |
| 4,978,807 | 12/1990 | Smith | 203/DIG. 6 |

Primary Examiner—Wilbur Bascomb, Jr.
Attorney, Agent, or Firm—Kenneth H. Johnson

[57] ABSTRACT

A method and apparatus for conducting a catalytic distillation process is provided which allows for maintaining a liquid level in selected portions of the catalyst bed. Three particular processes disclosed are the production of methyl tertiary butyl ether, tertiary butyl alcohol and cumene.

9 Claims, 2 Drawing Sheets

METHOD FOR OPERATING A CATALYTIC DISTILLATION PROCESS

This is a division of application Ser. No. 07/328,478, filed Mar. 23, 1989.

BACKGROUND OF THE INVENTION

1. Field of the invention

The present invention relates to an improvement in the manner of conducting concurrent reactions and distillations wherein the catalyst is also the distillation structure.

2. Related art

Recently a new method of carrying out catalytic reactions has been developed, wherein the components of the reaction system are concurrently separable by distillation, using the catalyst structures as the distillation structures. This method is now generally known as catalytic distillation and any reference to catalytic distillation herein will be taken to mean this method or process. Such systems are described variously in U.S. Pat. Nos. 4,215,011; 4,232,177; 4,242,530; 4,302,356; 4,307,254; 4,336,407; 4,439,350; 4,443,559; and 4,482,775 commonly assigned herewith.

Briefly, a preferred and commercial catalyst structure described in the above patents comprises a cloth belt with a plurality of pockets spaced along the belt and containing particulate catalyst material, said cloth belt being wound in a helix about a spacing material such as stainless steel knitted mesh. These units are then disposed in the distillation column reactor. In addition, commonly assigned U.S. Pat. Nos. 4,443,559 and 4,250,052 disclose a variety of catalyst structures for this use and are incorporated herein.

The success of catalytic distillation lies in an understanding of the principles associated with distillation. First, because the reaction is occurring concurrently with distillation, the initial reaction product is removed from the reaction zone as quickly as it is formed. The removal of the reaction product minimizes further reaction, decomposition, polymerization and the like. Second, because in a distillation the compounds are boiling, the temperature of the reaction is controlled by the boiling point of the mixture at the system pressure. The heat of the reaction simply creates more boil up, but no increase in temperature. Third, the reaction has an increased driving force because the reaction products have been removed and cannot contribute to a reverse reaction (Le Chatelier's Principle).

The distillation parts of the above disclosures have been conventional, i.e., counter-current vapor liquid flow in the packed catalyst bed with the catalyst acting as the contact structure, at least in the reaction zone. The reaction zone having the catalyst packing is designated the reaction distillation zone to distinguish it from other distillation zones which contain either inert packing or conventional distillation trays. The conventional distillation zones may be above or below the distillation reaction zone according to the separation desired.

In one particular embodiment for making methyl tertiary butyl ether, the physical embodiment of the distillation column reactor includes a separate distillation zone below the distillation reaction zone to insure that the unreacted feed components are removed from the ether product which is taken off as bottoms product. In at least one case the lower distillation zone is a separate distillation column connected to another distillation column which contains the catalyst. Vapor and liquid flow lines are provided so that essentially the two columns act as one.

Because of the nature of the distillation the reactants and products are separated. Depending upon the components, however, the reactants may be separated before the desired reaction is completed requiring recycle. It was thus seen to be desirable to retain the reactants in contact with the catalyst while still separating out the products.

SUMMARY OF THE INVENTION

Briefly the present invention is the discovery that the reaction rate can be increased by improving the contact of the liquid with the catalyst, which is accomplished by increasing the liquid level in the reaction distillation zone This is achieved by a liquid flow restrictor between the distillation reaction zone and the lower distillation zone. That is, the vapor from below may rise up to (and through) the reaction distillation zone as in a conventional or prior operation but a portion of the liquid is maintained there. If a single distillation column reactor is used, a conventional distillation tray with the downcomer area blocked is located between the reaction distillation zone and the distillation zone. A by pass line for liquid flow is provided about the tray and a valve is provided in the liquid flow conduit to restrict liquid downflow and thereby to build up a liquid level above that tray just below the catalyst bed. Alternatively a perforated plate may be used to support the catalyst and cause a liquid pressure drop in the column thus building up a level in the catalyst. If the two column system is used, then a valve or other restriction means is placed in the liquid flow line between the two columns.

While the particular position of the liquid level has been described above to be at the lower end of the distillation reaction zone, it could just as easily be placed anywhere in the catalyst bed depending upon the desired reactions.

The term "liquid level" is used herein to mean an increased density of the material in the reaction distillation zone over that of a pure distillation as distinguished from a continuous liquid phase. The phase system as present in the reaction distillation zone is physically a froth. This is the result of the vapor traveling up through the liquid retained in the zone.

Another way of viewing this is that in normal distillation there is a vapor with liquid (internal reflux) trickling down through the vapor and contacting the catalyst whereas in the present "flooded" system the vapor is traveling up through a liquid phase to create the froth or foam.

Hence in essence the benefits of the distillation are still obtained, i.e., separating the various components by the distillation whereas the increased liquid volume in contact with the catalyst improves the synthesis reaction.

DETAILED DESCRIPTION OF THE PREFERRED EMBODIMENTS

Referring now to the Fig.s a detailed description of the preferred embodiments can be appreciated.

Figure 1:
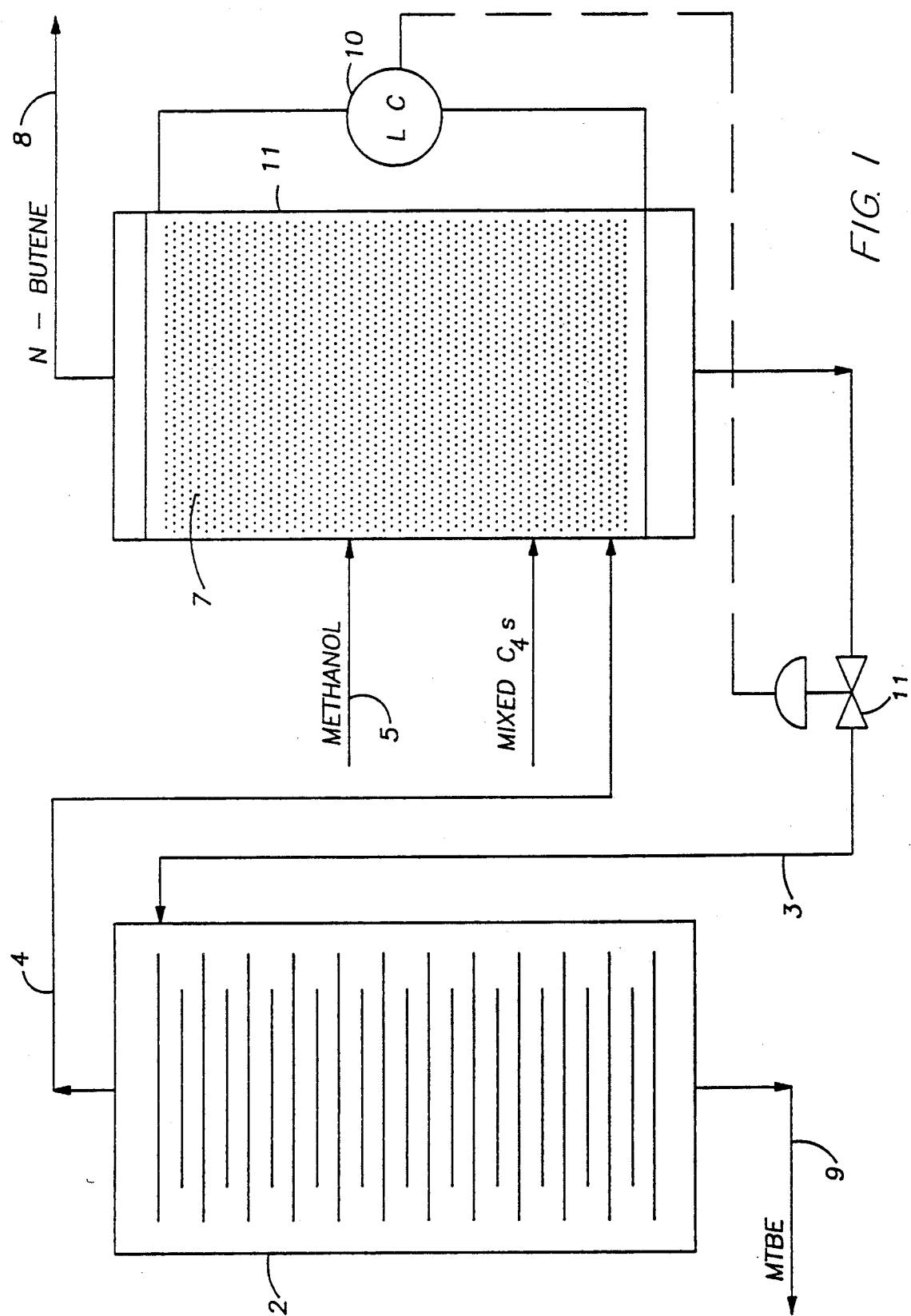
FIG. 1 is a flow diagram of one embodiment of the invention showing separate columns for the distillation and reaction zones.

FIG. 1 shows a simple flow diagram of a process using the present invention. The particular process shown is for the production of methyl tertiary butyl ether (MTBE) from the reaction of methanol and isobutene in a mixed butene/butane feed stream. For a detailed description of the process the reader is referred to U.S. Pat. No. 4,307,254 which is herein incorporated by reference. Generally there is shown a first distillation column 1 which contains an acid cation exchange resin packing 7 suitable for the reaction. The acid cation exchange resin catalyst 7 is suitably disposed in the column 1 as described in U.S. Pat. No. 4,307,254 to act as both a catalyst and distillation structure. The methanol and mixed butene/butane stream is fed to the first column 1 into the catalyst 7 in a feed zone via flow lines 5 and 6. The methanol reacts with the isobutene in the catalyst bed or reaction distillation zone to form MTBE. The unreacted components of the mixed butene/butane stream are distilled off overhead and recovered via flow line 8. At the same time the MTBE product is distilled off toward the bottom since the temperature of the catalyst (reaction distillation) zone is maintained at the boiling of the reactants at the operating pressure of the column, which is lower than the boiling point of the MTBE.

The bottoms liquid product containing MTBE and some dissolved unreacted methanol and $C_4$ hydrocarbons is carried out the bottom of the first column 1 via flow line 3 to the top of second column 2 where the MTBE is more completely separated from any dissolved methanol or $C_4$'s in a conventional distillation column 2 having trays as shown or inert packing and recovered via flow line 9. The unreacted materials are recovered overhead via flow line 4 which carries them back as vapors to the bottom of the first column 1. A level controller 10 is secured to the first column 1 and senses a liquid level in the first column 1 (as by a differential pressure) and operates flow control valve 11 which acts as a liquid flow restriction between the two columns and maintains a desired preset liquid level in the catalyst bed 7 of column I. Note the level control 10 may be positioned to detect the level over any portion of the column 1.

Pumps, compressors, and other operating equipment are not shown as they are conventional and readily selected by those of ordinary skill in the art of distillation column design. Example I shows a comparison of one such unit operated with and without the liquid level in the catalyst bed.

Figure 2:
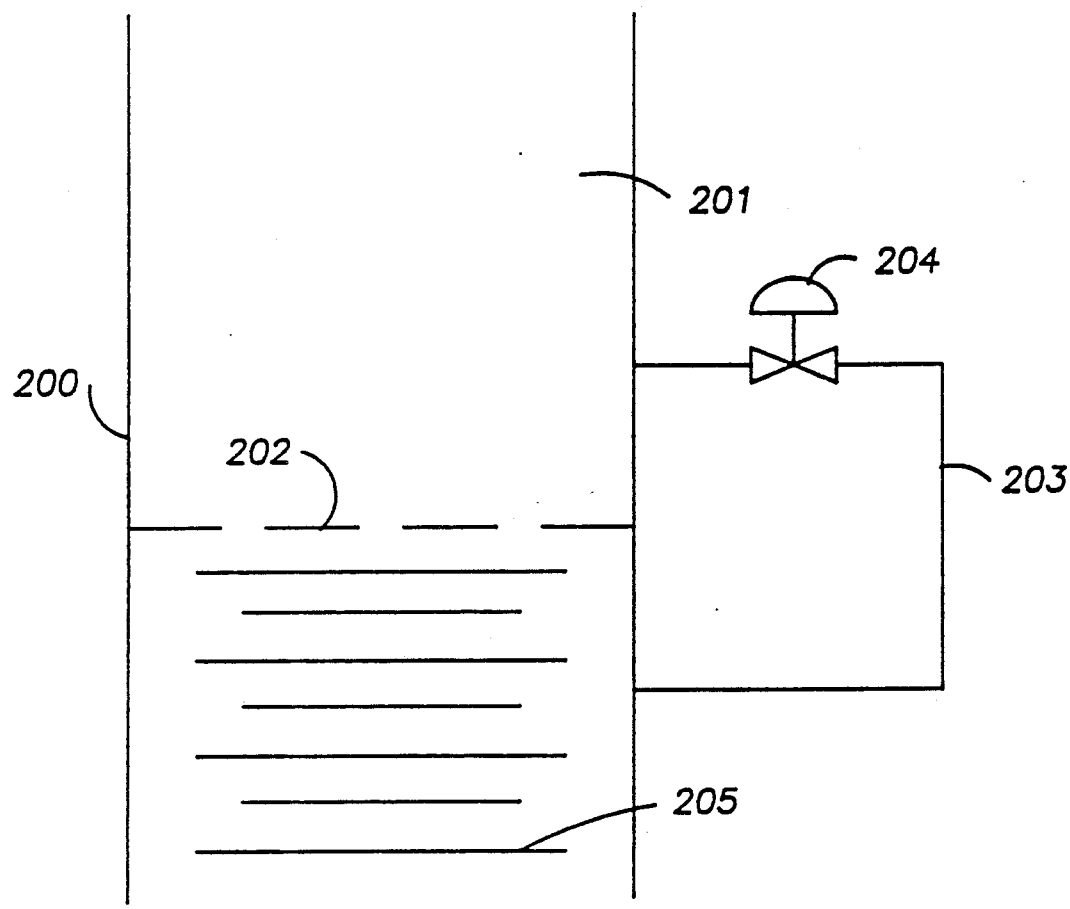
FIG. 2 is a plan view of the liquid flow restriction in a single column.

FIG. 2 illustrates an arrangement which may be used if only one column is used. Only that portion of the column is illustrated that is used to maintain the liquid level in the catalyst bed.

Figure 3:
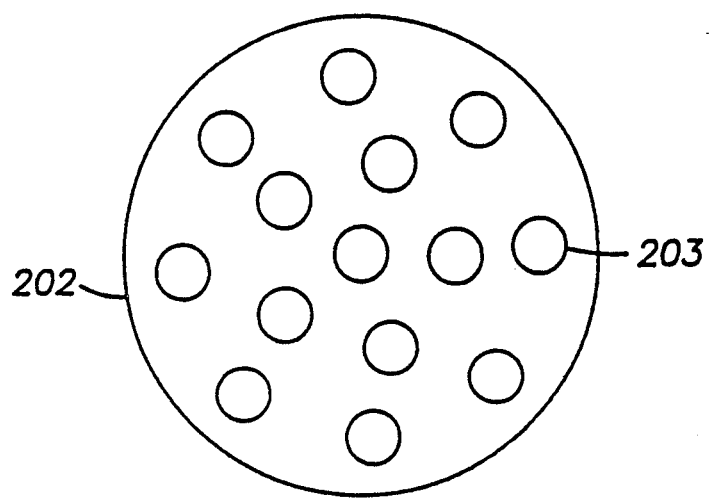
FIG. 3 is top view of a perforated plate useful in the column of FIG. 2.

In FIG. 2 the column 200 has a bed of catalyst 201 which acts as a distillation structure. Directly below the catalyst bed 201 is shown a perforated plate 202 which supports the catalyst bed 201. The plate 202 as indicated in FIG. 3 is perforated to allow gas passage upward into the catalyst bed 201 yet provides a sufficient pressure drop to allow a liquid level to build up above the plate in the bed 201. The plate is approximately 5–20 percent open space. A liquid bypass flow line 203 is provided about the plate 202 to give added control of the level.

Valve 204 in bypass 203 may be opened or closed in response to a differential pressure (indicating liquid level) to control the liquid level. If desired the valve can be part of a control loop (not shown) responding to a liquid level controller.

Alternatively a standard distillation tray may be substituted for the perforated plate 202. The downcomer area of the standard tray is blocked and the by pass flow line 203 used to control the liquid level in the bed.

EXAMPLE I

A commercial catalytic distillation process for the production of MTBE was operated according to that disclosed in U.S. Pat. No. 4,307,254. Following an incident in which the catalyst was partially deactivated, the operation was changed to maintain the liquid level at the top of the catalyst zone. The arrangement was similar to that shown in FIG. 1. A control valve acted as a restriction in the liquid flow line 3 to control the liquid level which was sensed by a differential pressure in the distillation reaction column 1. Unexpectedly, the performance of the commercial unit with the damaged catalyst was almost equal to the unit with undamaged catalyst.

EXAMPLE II

The method and structure have been found to be particularly useful for conducting the catalytic distillation production of tertiary butyl alcohol (TBA) from the hydration of isobutylene. In the TBA process a stream containing isobutylene is fed to the column below the catalyst bed and water is fed above the catalyst bed. The catalyst bed contains an acid cation exchange resin as described in U.S. Pat. No. 4,307,254 and is placed into the one inch laboratory column in the manner described therein. Unreacted butylene, water and inerts (such as other $C_4$'s) are taken overhead and the TBA product is recovered as bottoms.

Water must be present in amounts sufficient to maintain the catalyst in a hydrated state plus enough for the reaction and to accommodate the water azeotropes in the system. One method of control is to measure the amount of water present in the TBA fraction within the column and to maintain that amount above zero but below the azeotropic concentration at the temperature and pressure used.

Without the liquid level, the catalyst performs satisfactorily at first but quickly loses its selectivity due to loss of water despite the control technique outlined above. This may be attributed to mass transfer and distribution problems within the catalyst bed. It has been found that maintaining a liquid level in the catalyst bed using the technique of FIG.S 2 and 3 maintains the wetted state of the catalyst and allows high selectivity toward tertiary butyl alcohol production. Table I below compares the results of the process with and without the liquid level in the bed. The liquid level in the catalyst bed is indicated by the high differential pressure across the bed. In the test runs, a 1″ diameter tower was used ten feet in length. Four feet of Rohm and Haas Amberlyst 15 catalyst was inserted into the column in a pocketed belt twisted with wire mesh.

Example III

In one other example the pilot plant was run as described in commonly assigned U.S. pat. appln. Ser. No. 122,485 filed Nov. 16, 1987 using a 3″ pilot plant column with Union Carbide LZY-82 molecular sieve in the pockets of the catalyst structure for the production of cumene from the alkylation of benzene with propylene. Again, the use of the liquid level as measured by the differential pressure across the bed improved performance of the catalyst and process. Table II below shows comparative data between the normal operation and with the liquid level.

While particular configurations have been shown, it should be understood that the liquid level may be maintained at any location within the catalyst bed using the techniques disclosed in either FIG.S 2 and 3.

The invention is claimed is:

1. A method for operating a catalytic distillation process, comprising the steps of:
    (a) introducing reactants into a feed zone of a distillation reaction column having an upper zone containing a catalytic distillation structure which defines a reaction distillation zone and a lower zone containing conventional inert distillation structure which defines a distillation zone;
    (b) simultaneously in said reaction distillation zone
        (1) reacting at least a portion of the reactants to form reaction products, and
        (2) separating the reaction products and/or reactants by fractional distillation;
    (c) restricting the downward flow of internal reflux between said reaction distillation zone and said distillation zone to maintain a liquid level above the restriction for additional contact and reaction of the liquid and distillation vapors, said liquid level being a froth characterized as having an increased density of the material in the reaction distillation zone compared to a distillation carried out in the absence of said froth.

2. The method of claim 1 wherein said lower distillation zone is contiguous to said upper reaction distillation zone.

3. The method of claim 1 wherein said lower distillation zone is separated from said upper reaction distillation zone and is in fluid communication therewith for vapor and liquid flows therebetween.

4. The method of claim 2 wherein said downward flow is restricted by a perforated plate and said liquid level is controlled by means of a by-pass line around said perforated plate, said by-pass line including a control valve responsive to said liquid level.

5. The method of claim 3 wherein said downward flow is restricted by a control valve in the liquid communication between said upper reaction distillation zone and said lower distillation zone, said control valve operating in response to said liquid level.

6. A method for operating a catalytic distillation process, comprising the steps of:
    (a) introducing reactants into a feed zone of a distillation reaction column having an upper reaction distillation zone containing a catalytic distillation structure and a lower distillation zone containing conventional inert distillation structure;
    (b) simultaneously in said upper reaction distillation zone
        (1) reacting at least a portion of the reactants to form reaction products, and
        (2) separating the reaction products and/or reactants by fractional distillation;
    (c) restricting the downward flow of internal reflux between said upper and lower zones to maintain a froth level in said upper zone having an increased density of the material in the reaction distillation zone compared to a distillation carried out in the absence of said froth; and
    (d) fractionating by fractional distillation reactants and/or reaction products in said lower distillation zone.

7. The method of claim 6 wherein the level of said froth is detected and controlled by the differential pressure across said reaction distillation zone compared to the differential pressure across said reaction distillation zone absent said froth.

8. A method for operating a catalytic distillation process, comprising the steps of:
    (a) introducing reactants into a feed zone of a distillation reaction column having an upper reaction distillation zone containing a catalytic distillation structure and a lower distillation zone containing conventional inert distillation structure;
    (b) simultaneously in said upper reaction distillation zone
        (1) reacting at least a portion of the reactants to form reaction products, and
        (2) separating the reaction products and/or reactants by fractional distillation;
    (c) measuring the differential pressure across said upper reaction distillation zone;
    (d) controlling the downward flow of internal reflux between said upper and lower zones in response to said differential pressure measurement to maintain a froth level in said upper zone having an increased density of the material in the reaction distillation zone compared to a distillation carried out in the absence of said froth; and
    (e) fractionating by fractional distillation reactants and/or reaction products in said lower distillation zone.

9. A method for operating a catalytic distillation process, comprising the steps of:
    (a) introducing reactants into a feed zone of a distillation reaction column having an upper zone containing a catalytic distillation structure which defines a reaction distillation zone and a lower zone containing conventional inert distillation structure which defines a distillation zone;
    (b) simultaneously in said reaction distillation zone
        (1) reacting at least a portion of the reactants to form reaction products, and
        (2) separating the reaction products and/or reactants by fractional distillation; and
    (c) restricting the downward flow of internal reflux between said reaction distillation zone and said distillation zone to maintain a liquid level above the restriction for additional contact and reaction of the liquid and distillation vapors, said liquid level being a froth characterized as having an increased density of the material in the reaction distillation zone compared to a distillation carried out in the absence of said froth; and
    (d) detecting and controlling said liquid level by the differential pressure across said reaction distillation zone compared to the differential pressure across said reaction distillation zone absent said froth.

* * * * *